United States Patent [19]

Ellis, Jr. et al.

[11] Patent Number: 5,212,300

[45] Date of Patent: May 18, 1993

[54] CYANO- AND POLYCYANOMETALLO-PORPHYRINS AS CATALYSTS FOR ALKANE OXIDATION

[75] Inventors: Paul E. Ellis, Jr., Downingtown; James E. Lyons, Wallingford, both of Pa.

[73] Assignee: Sun Company, Inc. (R&M), Philadelphia, Pa.

[21] Appl. No.: 892,107

[22] Filed: Jun. 2, 1992

Related U.S. Application Data

[63] Continuation-in-part of Ser. No. 758,148, Sep. 12, 1991, Pat. No. 5,118,886.

[51] Int. Cl.$^5$ .......................................... C07D 487/22
[52] U.S. Cl. .......................................................... 540/145
[58] Field of Search ........................................ 540/145

[56] References Cited

U.S. PATENT DOCUMENTS

| | | | |
|---|---|---|---|
| 4,895,680 | 1/1990 | Ellis et al. | 260/410.9 |
| 4,895,682 | 1/1990 | Ellis et al. | 260/410.9 |
| 4,900,871 | 2/1990 | Ellis et al. | 568/399 |
| 4,970,348 | 11/1990 | Ellis et al. | 568/399 |
| 5,118,886 | 6/1992 | Ellis et al. | 568/910 |

OTHER PUBLICATIONS

Yamaguchi et al., Inorg. Chem. (1992) 31, 3216–3222.
Kadish et al., Inorg. Chem. (1985), 24, 2148–2156.
P. E. Ellis, Jr. and J. E. Lyons, Catalysis Letters, 8, 45 (1991).
H. J. Callot, (1) Bull. Soc. Chim. de France 1974 No. 7–8, pp. 1492–1496.

Primary Examiner—Marianne M. Cintins
Assistant Examiner—John Peabody
Attorney, Agent, or Firm—Q. Todd Dickinson; Donald R. Johnson; Stephen T. Falk

[57] ABSTRACT

New compositions of matter comprising cyano-substituted metal complexes of porphyrins are catalysts for the oxidation of alkanes. The metal is iron, chromium, manganese, ruthenium, copper or cobalt. The porphyrin ring has cyano groups attached thereto in meso and/or $\beta$-pyrrolic positions.

7 Claims, No Drawings

CYANO- AND POLYCYANOMETALLO-PORPHYRINS AS CATALYSTS FOR ALKANE OXIDATION

The Government of the United States of America has rights in this invention pursuant to Cooperative Agreement No. DE-FC21-90MC26029 awarded by the U. S. Department of Energy.

This application is a continuation-in-part of application Ser. No. 07/758148, filed Sep. 12, 1991, issued Jun. 2, 1992 as U.S. Pat. No. 5,118,886.

BACKGROUND OF THE INVENTION

This invention relates to metalloporphyrins useful as catalysts for the oxidation of alkanes, and more particularly to metalloporphyrins containing cyano groups on the porphyrin ring.

Cyano-substituted metalloporphyrins are known in the art, H. J. Callot, "Bromation de la m-tetraphenyl-porphine. Preparation d'alkyl - et de polycyanoporphines (1), Bull. soc. chim. de France 1974, No. 7-8, pages 1492-1496, discloses copper complexes of meso-tetraphenylporphyrins having cyano substituents on one, two, three and four of the pyrrolic rings. R. J. Donohoe, M. Atamian and D. F. Bocian, "Characterization of Singly Reduced Iron (II) Porphyrins", J. Am. Chem. Soc., 1987, 109, 5593-5599, disclose Fe(II)2,7,12-tricyano-5,10,15,20-tetraphenylporphyrin and Fe-(II)2,7,12,17-tetracyano-5,10,15,20-tetraphenylporphyrin.

DESCRIPTION OF THE INVENTION

We have discovered novel cyano-substituted metalloporphyrins which contain cyano groups in meso and/or beta positions of the porphyrin ring.

The atoms or groups on the meso positions of a metalloporphyrin are represented by the X's in the following structural formula, and the atoms or groups on the β-pyrrolic, or beta, positions by the Y's:

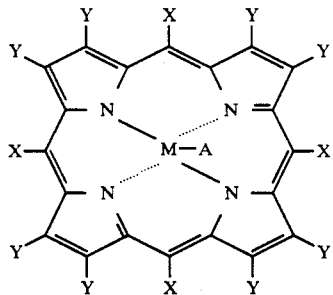

where M is metal, A (1) is an anion such as chloride, bromide, fluoride, cyanide, azide, nitride, thiocyanate, cyanate, hydroxy, methoxy, chlorate, carboxylates such as acetate, propionate and benzoate, or (2) is absent, which compounds include iron complexes of μ oxo dimers wherein two structures as shown in said formula are joined through an M-O-M linkage.

METAL COMPLEXES OF MESOCYANOPORPHYRINS

In one embodiment of the invention, the metalloporphyrin has one or more cyano groups in meso positions and has, in beta positions, either hydrogen atoms, H, or halogen atoms such as fluorine, chlorine or bromine, or nitro or cyano groups, or a hydrocarbon group or a halocarbon group. Examples of halocarbon groups are haloalkyl groups such as perfluoromethyl, perfluoroethyl and the like and haloaryl groups such as perfluorophenyl and the like. Examples of hydrocarbon groups are aryl groups such as phenyl, substituted phenyl and the like, and alkyl or cycloalkyl groups such as methyl, ethyl, cyclohexyl and the like.

In this embodiment, 1 to 4 of the X's in the above formula are CN, 0 to 3 of said X's are hydrogen, halogen, hydrocarbon or halocarbon, and Y is hydrogen, nitro, cyano, halogen, hydrocarbon or halocarbon. The Y's may all be one atom or group, or different atoms or groups This embodiment differs from the meso-tetraphenyl cyanoporphyrins of the prior art in having cyano groups in meso positions of the metalloporphyrin complex.

METAL COMPLEXES OF BETACYANOPORPHYRINS

In another embodiment of the invention, the metalloporphyrin has one or more cyano groups in beta positions, and hydrogen or a substituent other than cyano in the remaining beta positions. The substituent may be halo, hydrocarbon or halocarbon. In this embodiment, X in the above formula is hydrogen, halogen, nitro, cyano, alkyl, cycloalkyl or halocarbon, at least one of said Y's is cyano and the remaining Y's are hydrogen, halogen, nitro, hydrocarbon or halocarbon.

This embodiment differs from the mesotetraphenyl-betacyanoporphyrins of the prior art in having different substituents in the meso positions.

In a preferred embodiment, the compound has either halogen atoms or cyano groups in all of the beta positions. In this embodiment, X in the above formula is hydrogen, halogen, nitro, cyano, hydrocarbon or halocarbon, at least one of the Y's is cyano, and the remaining Y's are halogen.

This embodiment differs from the metal complexes of mesotetraphenylbetatetracyanoporphyrin of the prior art in having halogen substituents in beta positions.

Substituents in the meso positions of the metalloporphyrins of this embodiment may be aryl groups such as phenyl, or they may advantageously be perhalocarbon groups such as perfluoromethyl, perfluoroethyl and the like. In this embodiment, X in the above formula is a perhalocarbon group, and Y is hydrogen or CN, at least one of the Y's being CN.

This embodiment differs from the metal complexes of mesotetraphenylnitroporphyrins of the prior art in having perhalocarbon groups in meso positions of the porphyrin ring.

In each embodiment of the invention, M in the above formula is preferably Fe, Cr, Mn, Ru, Cu or Co, more preferably Fe.

The compounds of the invention are useful for example as catalysts in the oxidation of organic compounds. The manner of usage of the compounds for this purpose is disclosed in applicants' copending application Ser. No. 07/58148, filed Sep. 12, 1991, issued Jun. 2, 1992 as U.S. Pat. No. 5,118,886, the disclosure of which is hereby incorporated by reference in this application.

The terms porphyrin, porphin and porphine are used interchangeably herein to refer to the structure shown in the structural formula supra.

The following examples illustrate the invention:

EXAMPLE 1

Preparation of $H_2P(CN)_4$ and $MP(CN)_4Cl$ $P=$Porphine $ZnP(NO_2)_4$, zinc meso-tetranitroporphine (100 mg), is dissolved in 100 ml of glacial acetic acid. At 90°–100° C., 0.5 g of KCN dissolved in 50 ml of tetrahydrofuran (THF) is dripped into the solution with stirring. The reaction is heated until TLC examination shows all of the starting material has reacted. The material is cooled, filtered and evaporated to dryness. The solid residue is washed thoroughly with water to remove excess KCN then dried and recrystallized from hot dichloromethane or chloroform/hexane. The zinc is removed during this process, leaving $H_2P(CN)_4$, meso-tetracyano-porphine. The metal salts of this complex are prepared by refluxing a THF solution of the $H_2P(CN)_4$ with the metal chloride ($MCl_2 \cdot xH_2O$ where M is Fe, Cr, Co, Mh or Ru) until the metal is inserted and purifying by either recrystallization or chromatography.

EXAMPLE 2

Preparation of Zn $TPPF_{20}\beta$-$Br_7CN$ and $ZnTPPF_{20}\beta$-$Br_6(CN)_2$ (TPP=Tetraphenylporphine)

100 mg of $ZnTPPF_{20}\beta$-$Br_8$ is dissolved in 90 ml of dimethylformamide. To this is added 129 mg of CuCN dissolved in 4.5 g of pyridine. The solution is stirred and refluxed for 5 hours then added to a saturated KCN solution. The porphyrin content is extracted with $CH_2Cl_2$ and evaporated to dryness in vacuo at 90° C. to remove the pyridine in addition to the $CH_2Cl_2$. After chromatography on silica gel two major bands are obtained other than some starting material. The first green band elutes from the column with $CHCl_3$. Both bands have infrared (KBr)$v_{c-n}$ around 2220 cm$^{-1}$. The first green material is identified as $ZnTPPF_{20}$ $\beta$-$Br_7CN$ and the second brown band as a mixture of isomers of $ZnTPPF_{20}$ $\beta$—$Br_6(CN)_2$.

The zinc is removed by treating a $CH_2CL_2$ solution of either of the cyano porphyrins with a few bubbles of HCl gas at room temperature followed by neutralization with bicarbonate solution. Complexes of metals such as Fe, Cr, Mn, Cu and Ru can be obtained by stirring the metal chloride ($FeCl_2$, $CrCl_2$, $CoCl_2$), or carbonyl ($Ru_3(CO)_{12}$) with the free porphyrin in hot dimethylformamide.

The invention claimed is:

1. A composition useful as a catalyst comprising the compound having the formula:

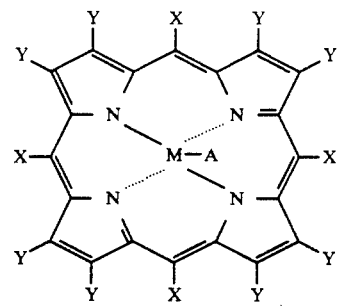

where M is iron, chromium, manganese, ruthenium, copper or cobalt, X is hydrogen, halogen, nitro, cyano, alkyl, cycloalkyl or halocarbon, at least one of said Y's is cyano the remaining Y's are hydrogen, halogen, nitro, cyano hydrocarbon or halocarbon, A is an anion selected from the group consisting chloride, bromide, fluoride, cyanide, azide, nitride, thiocyanate, cyanate, hydroxy, methoxy, chlorate, carboxylate, or is absent, said compounds including iron complexes of $\mu$ oxo dimers comprising two structures as shown in said formula joined through an M-O-M linkage.

2. Composition according to claim 1 wherein said remaining Y's are halogen.

3. Composition according to claim 1 wherein each X is fluorocarbon.

4. As a new composition of matter, useful as a catalyst, an iron complex of mesotetrafluoroalkylbetacyanoporphyrin or mesotetrafluoroalkylbetacyanoporphyrin halide, having 1 to 7 carbon atoms in said alkyl group.

5. A metal complex of mesotetraphenyl $\beta$-heptabrom $\beta$- cyanoporphine, where said metal is iron, chromium, manganese, ruthenium, copper or cobalt.

6. A metal complex of mesotetraphenyl $\beta$-hexabromo $\beta$-dicyanoporphine, where said metal is iron, chromium, ruthenium, copper or cobalt.

7. A composition according to claim 1 wherein said compound is said iron complex of $\mu$ oxo dimer.

* * * * *